(12) United States Patent
Harazin et al.

(10) Patent No.: US 7,353,688 B2
(45) Date of Patent: Apr. 8, 2008

(54) METHODS AND SYSTEMS FOR DETERMINING A POSITION OF A PROBE

(75) Inventors: Richard Raymond Harazin, Lombard, IL (US); Ronald Alvin Zweifel, Naperville, IL (US)

(73) Assignee: PerkinElmer LAS, Inc., Waltham, MA (US)

( * ) Notice: Subject to any disclaimer, the term of this patent is extended or adjusted under 35 U.S.C. 154(b) by 0 days.

(21) Appl. No.: 11/268,867

(22) Filed: Nov. 8, 2005

(65) Prior Publication Data

US 2006/0096396 A1    May 11, 2006

Related U.S. Application Data

(60) Provisional application No. 60/522,808, filed on Nov. 9, 2004.

(51) Int. Cl.
*G01B 7/00* (2006.01)
*G01F 25/00* (2006.01)

(52) U.S. Cl. ............... 73/1.74; 73/1.79; 73/863.01; 702/94; 702/150

(58) Field of Classification Search ........ 73/1.73–1.74, 73/863.01, 1.79, 866.5; 702/94–95, 150, 702/152, FOR. 169
See application file for complete search history.

(56) References Cited

U.S. PATENT DOCUMENTS

| 4,523,382 A | * | 6/1985 | Werner et al. | ............... 33/556 |
| 5,432,503 A | * | 7/1995 | Pekar | ......................... 340/680 |
| 5,929,643 A | * | 7/1999 | Sakai et al. | ................ 324/750 |
| 6,076,953 A | * | 6/2000 | Oakley | ..................... 700/195 |

* cited by examiner

*Primary Examiner*—Thomas P. Noland

(57) ABSTRACT

The present methods and systems include aligning at least two sensors with one or more known locations, selecting at least two of the at least two sensors, electrically driving the probe, based on signals received by the selected sensors, determining whether the probe is aligned with the known location(s), and, optionally adjusting the probe position based on the determination. The methods and systems also include repeatedly returning to electrically driving and positioning the probe until the probe is aligned with the selected sensors, and/or repeatedly returning to selecting at least two of the at least two sensors. The relative position of the probe with respect to the selected sensors may also be determined.

17 Claims, 9 Drawing Sheets

METHODS AND SYSTEMS FOR DETERMINING A POSITION OF A PROBE

CLAIM OF PRIORITY

This application claims priority to U.S. Ser. No. 60/522,808, and filed on Nov. 9, 2004, the contents of which are herein incorporated by reference in their entirety.

BACKGROUND (1) Field

The disclosed methods and systems relate generally to determining a position of a probe, for example, positioning of pipettes in liquid handling and/or liquid level sensor systems.

(2) Description of Relevant Art

Probes can be used in many different types of systems, including for example, liquid level sensing systems, where a pipette can be used as a probe to aspirate and/or dispense a liquid from and/or to a container (e.g., a well in a multi-well plate). Recent advancements in such systems focus on the challenge of withdrawing and/or dispensing precise small volumes of a liquid using a pipette without contaminating the liquid. Several manual and automated liquid-measuring systems are available for this purpose.

In several of these systems, a pipette probe is movably mounted over a container (e.g., well in a multi-well plate), and vertically lowered into the container until the tip of the probe/pipette reaches a desired level below or above the upper surface of the liquid (the meniscus). An amount of liquid may then be withdrawn from or dispensed into the container.

A consideration in liquid level sensing is properly positioning the pipette as it is lowered into a container. Generally, in a liquid handling embodiment, a cantilevered arm that includes one or more pipette tips is moved over and/or substantially parallel to one or more wells of a multi-well plate before moving in a direction that is substantially orthogonal to the wells to allow for aspiration and/or dispensing as provided herein. In some embodiments, an individual pipette may have contact with one, more than one, and/or all of the wells in the plate. Because a cantilevered arm may present variation in one, two, or three directions and/or dimensions along the arm, and further because the coordinate system of the arm is generally not aligned with the coordinate system associated with the multi-well plate, difficulties can arise when aspirating and/or dispensing.

SUMMARY

The present teachings include methods and systems for determining a position of a probe, which can include aligning a probe with a known point. The methods and systems include distributing an electrical signal to the probe, positioning at least two sensors in electrical communication with the electrical signal from the probe, generating an electrical signal at the two sensors based on electrical communication with the probe, and, determining the position of the probe relative to the two sensors based on the generated signals. The position of the probe with respect to the selected sensors may also be determined. The position can be determined by generating a sum signal based on the sum of the generated electrical signals at the at least two sensors.

The present methods and systems include determining the position of the probe by associating the two sensors with a coordinate system, identifying at least two sensors positioned along at least one of the axes of the coordinate system, and generating a sum signal based on the sum of the generated electrical signals associated with the at least two identified sensors. In an embodiment, the coordinate system is multi-dimensional.

The methods and systems also include determining the position by generating a difference signal based on the difference of the electrical signals at the two sensors. Accordingly, determining the position can include associating the sensors with a coordinate system, identifying at least two sensors positioned along at least one of the axes in the coordinate system, generating a sum signal based on the sum of the generated electrical signals associated with the identified at least two sensors, generating a difference signal based on the difference of the generated electrical signals associated with the identified two sensors, and, determining the position of the probe by comparing the sum signal and the difference signal. Determining the position by comparing can include attenuating the sum signal and/or adjusting the DC offset of the sum signal. In some embodiments, the methods and systems include providing at least one output indicative of which of the identified two sensors the probe is nearest. The methods and systems can include adjusting the position of the probe based on the determined probe position.

In one embodiment, the two or more sensors include a capacitive sensor and/or are in electrical communication with a printed circuit board. The probe can be configured to travel substantially orthogonal to a plane containing the printed circuit board. The printed circuit board can include an orifice for receiving the probe, and in an embodiment, the probe is a pipette. The system can be a liquid level sensing system.

Prior to distributing the electrical signal to the probe, the methods and systems can include aligning the two sensors with a known location, such as, for example, a well, container, or other known location.

When the position of the probe is determined, the methods and systems can include extrapolating the determined position to at least one other location in a coordinate system associated with the two sensors and/or a coordinate system associated with the probe. Accordingly, because a probe may not be positioned and/or aligned with one adjustment, the methods and systems can include repeatedly returning to distributing the electrical energy, etc., until the probe is aligned/positioned with the two or more sensors.

Also presented are systems for determining a position of a probe, including a source of energy to apply an electrical signal to the probe, at least two sensors in electrical communication with the electrical signal, and, at least one control for adjusting the position of the probe based on a comparison of signals generated from the at least two sensors and the relative distance between the at least two sensors. The control can include at least one processor to provide commands to adjust the position of the probe. Also included may be a signal processing scheme to compute a difference signal and sum signal using signals from the two or more sensors, at least one of which may be a capacitive sensor. The system can be a liquid level sensing system, and the probe may be a pipette.

The two sensors can be in electrical communication with a printed circuit board, which in some embodiments, includes an aperture for accepting the probe and/or for aligning the two or more sensors.

The present teachings also include methods that include aligning at least two sensors with a known location, selecting at least two of the at least two sensors, electrically driving the probe while the probe is moved towards the at least two sensors, based on signals received by the selected sensors, determining whether the probe is aligned with the known location and/or computing the location of the probe relative to the at least two sensors, and, potentially adjusting the probe position based on the determination. The methods and systems also include repeatedly returning to electrically driving and positioning the probe until the probe is aligned with the selected sensors, and/or repeatedly returning to selecting at least two of the at least two sensors.

The methods and systems include aligning at least two sensors with at least one known location, selecting at least two of the at least two sensors, electrically driving the probe, based on signals received by the selected sensors, determining whether the probe is aligned with the at least one known location, and, adjusting the probe position based on the determination. As provided herein, the methods and systems can also include repeatedly returning to electrically driving until the probe is aligned with the selected sensors, and/or repeatedly returning to selecting at least two of the at least two sensors. The determining can include computing a location of the probe relative to the at least two sensors. The probe can be electrically driven while the probe is moved towards the at least two sensors.

Other objects and advantages will become apparent hereinafter in view of the specification and drawings.

DESCRIPTION

Figure 1:
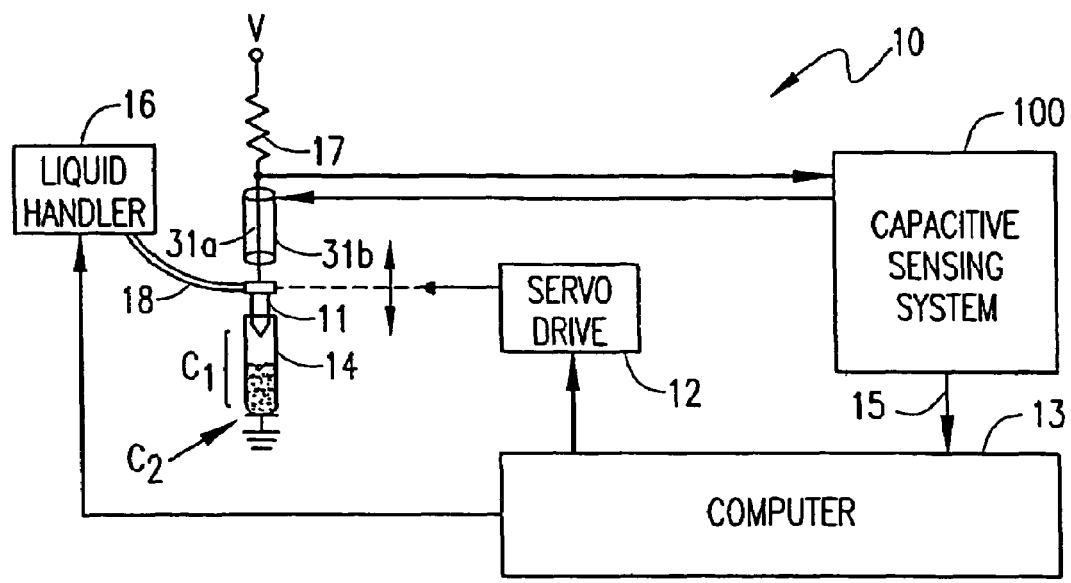
FIG. 1 is an example embodiment of a liquid handling system.

To provide an overall understanding, certain illustrative embodiments will now be described; however, it will be understood by one of ordinary skill in the art that the systems and methods described herein can be adapted and modified to provide systems and methods for other suitable applications and that other additions and modifications can be made without departing from the scope of the systems and methods described herein.

Unless otherwise specified, the illustrated embodiments can be understood as providing exemplary features of varying detail of certain embodiments, and therefore, unless otherwise specified, features, components, modules, and/or aspects of the illustrations can be otherwise combined, separated, interchanged, and/or rearranged without departing from the disclosed systems or methods. Additionally, the shapes and sizes of components are also exemplary and unless otherwise specified, can be altered without affecting the scope of the disclosed and exemplary systems or methods.

The present methods and systems relate to determining a position of a probe, which can include aligning a probe with a known location. Although the illustrated embodiments employ a liquid handling system for demonstration where pipette tips are used as a probe(s), it can be understood that such systems are for illustration and not limitation, and that the methods and systems have wide applicability to other systems and/or methods for measuring and/or determining a position of a probe and if necessary, altering the position of the probe, for example, to provide an alignment. As related to liquid handling systems, the present teachings allow for one or more pipettes to be aligned with containers and/or wells with which the pipette tip(s) may have one or more interactions, such that the coordinate system of the arm containing the pipette(s) may be at least partially aligned with the coordinate system associated with the container(s). The present methods and systems allow for such alignment without contact (e.g., non-contact) between a probe/pipette and/or a container/well using sensors to enable positioning of the probe in one, two, three, or more dimensions prior to the probe making contact with a container/well. The sensors are positioned to detect the probe/pipette as it moves substantially in a direction (e.g., substantially vertical direction) that allows for contact with a container/well. The description herein which employs a liquid handling system to demonstrate the present methods and systems shall also use an embodiment that includes a multi-well plate (e.g., "container"), although it can be understood that the use of "well" or "container" is for convenience with relation to the illustrated embodiments, and therefore use of such nouns can be understood generally to include a "known location" for which the coordinates of such location are known. It can thus be understood that in some embodiments, the methods and systems can be used to determine the location of a probe based on the location of the sensors relative to a known location, where in such embodiments, positioning and/or aligning the probe may not be performed.

FIG. 1 shows an embodiment of a liquid handling system. As FIG. 1 indicates, a liquid measuring system 10 can provide control of the position of a probe/pipette over one or more containers 14. For convenience, movement into and/or out of a well 14 can be understood to be movement in a substantially vertical or "z-axis" direction, and can be controlled by, for example, a servo-drive 12 such as shown in the illustrated embodiment, although other drivers can be used. In the FIG. 1, system, the servo is controlled by a processor 13 which determines the position of the pipette 11 relative to the well/container 14. In embodiments, the processor 13 can control a liquid handler 16 such as a syringe to aspirate and/or dispense in accordance with the embodiment from a container 14 through the pipette/probe 11 using a flexible tube 18.

In systems such as the example system of FIG. 1, a voltage at the probe 11 may be initially held at zero volts via a switch (not shown) between ground and a first conductor 31A that can be, for example, the inner conductance of a coaxial cable. The switch can be opened so that a voltage, V, can be applied through an impedance 17 to the probe, which has a capacitance, C1, such that the impedance 17 and the probe capacitance C1 provide an RC time constant. A second conductor 31B can be a shield of the coaxial cable which can be electronically driven at the same voltage as the first conductor 31A. It can be understood that the FIG. 1 embodiment is one illustrative system for liquid handling and is presented for illustration of the present methods and systems, and not limitation thereof. For example, although FIG. 1 shows one probe/pipette 11 and one well/container 14, it can be understood that the present methods and systems can be applied to systems having multiple probes and/or containers, and that alternative voltage or "driving" mechanisms may be used to apply a voltage to a probe 11. It can also be understood that other control mechanisms (e.g., servo 12 and/or processor 13) can be used, although such variations are merely some variations that may be included in the present teachings. Further, embodiments outside the scope of liquid handling systems are templated by the present teachings, with the illustrated embodiments provided merely for example.

Figure 2:
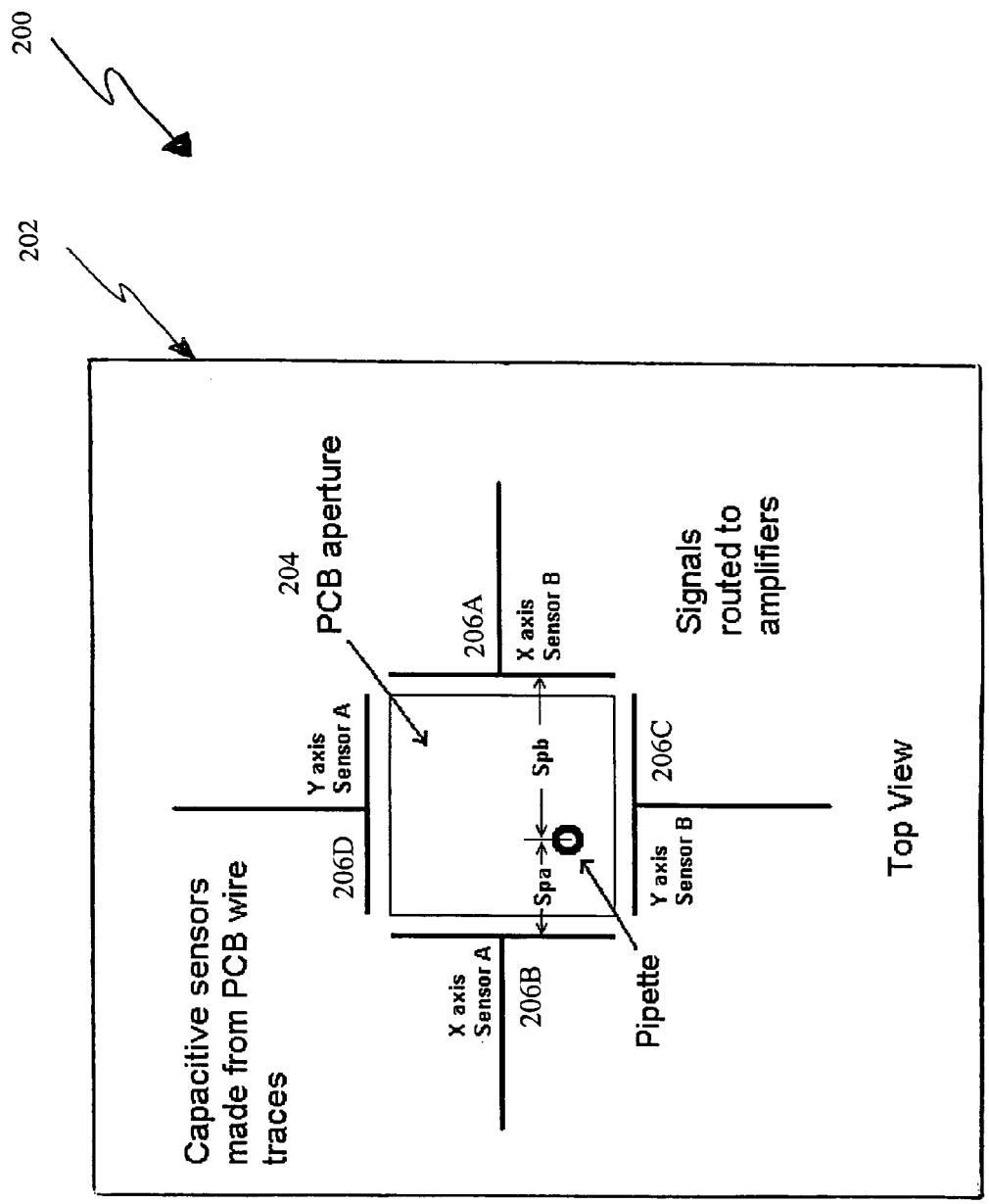
FIG. 2 shows one embodiment for positioning sensors relative to a known location.

As provided herein, the present methods and systems allow for the determination of a pipette/probe position based on measurements of the probe in one, two, three, or more dimensions, by sensors that are positioned to detect the probe, in some embodiments, while the probe is moving substantially in a direction that allows for contact with a known location (e.g., well/container), where in the illustrated embodiments, such direction can be understood to be a substantially vertical direction. FIG. 2 thus provides a first embodiment 200 where a printed circuit board (PCB) 202 can be provided with an aperture(s) 204 and sensors 206A, 206B, 206C, 206D aligned along the aperture(s) 204 in at least one dimension and/or axis of the plane containing the aperture 202. In the illustrated embodiment, the sensors 206A-D are capacitive sensors, although other sensors may be used. For the FIG. 2 embodiment, the size of the aperture 204 may be reduced to reduce edge effects within the capacitive sensors 206A-D. Further, in the FIG. 2 embodiment, the aperture(s) 204 of the PCB 202 is aligned with one or more wells 14 to allow alignment therewith. The FIG. 2 embodiment also shows sensors aligned in a first direction 206A, 206B and along a second direction 206C, 206D. It can be understood that sensors can be aligned along only one dimension, or optionally along further dimensions based on the embodiment. Further, although the FIG. 2 embodiment provides apertures 204 and sensors 206A-D mounted with a PCB 202, it can be understood that other embodiments may use other schemes for mounting the sensors 206A-D in a manner that provides an aperture 204 aligned with the container/well 14. Some sample embodiments may allow for the positioning of sensors 206A-D to be configured in a manner that allows for alignment with the known location, without requiring a PCB mounting and similarly, without requiring an aperture. For the FIG. 2 system which does employ an aperture and PCB, sensor output signals can be transmitted via one or more PCB wire traces to a signal processing scheme.

With continued reference to FIG. 1 and the embodiment of FIG. 2, the PCB 202 can be understood to be positioned between a container/well 14 and a pipette/probe 11 such that, when in the illustrated embodiment, a pipette 11 moves in a substantially vertical direction, the pipette 11 travels through the PCB aperture 202 and towards the well 14. It can thus be understood that in some embodiments, the aperture 204 can be sized to allow for a pipette 11 to travel through the aperture 204, although such may not occur in all embodiments. Again with reference to the FIG. 2 embodiment, as movement of the pipette 11 in the substantially vertical direction occurs (e.g., substantially orthogonal to the plane containing the PCB 202), the aforementioned switch can be controlled to electrically drive the pipette 11 based on voltage V.

The amount of voltage V can depend upon the material of the pipette 11, the sensitivity of the sensors 206A-D, and/or the type of sensor 206A-D, for example. In the FIG. 2 embodiment, the illustrated capacitive sensors 206A-D use air as a dielectric, although other sensor types (e.g., non-capacitive and/or other dielectric, etc.) may be used. In the FIG. 2 embodiment, a voltage V with an amplitude of twenty-four volts, for example, may be used.

It is known that current through a capacitor increases with change in voltage, and accordingly, for the FIG. 2 embodiment, the signal detected by the capacitive sensors 206A-D may increase with greater changes in pipette signal voltage. It can be further understood that the voltage V can be controlled via a switch, for example, to provide a specific frequency and/or slew rate to allow for detection by the sensors 206A-D. For example, in one embodiment, a frequency of 2 KHz can be used with a sawtooth waveform having a 10 microsecond pulse width (e.g., 2% duty cycle), although such example is provided for illustration and not limitation.

Returning to FIG. 2, as a pipette 11 approaches the aperture 204, the sensors 206A-D can detect the pipette 11 by detecting energy from the pipette 11 during voltage driving cycles, and the sensors 206A-D may thus generate a signal based thereon. As previously provided herein, such a signal(s) can be provided to, for example, a processor (e.g., processor 13) or other processing scheme that can compute a relative position of the pipette 11 relative to the sensors 206A-D and/or the aperture 202. Based on the position of the pipette 11, a processor 13 may provide data to a servo 12 that may alter the pipette position/alignment in one, two, or more axes and/or directions to allow for alignment of the pipette 11 with the sensors 206A-D, and hence, the aperture 204. In the FIG. 2 embodiment, a desired pipette-to-aperture/sensor alignment includes positioning and/or aligning a pipette 11 substantially in the center of the aperture/sensors, although it can be understood that other embodiments may have other alignments based on the positioning of the apertures/sensors relative to the known location(s) (e.g., containers/wells) and/or the pipette(s).

Figure 3:
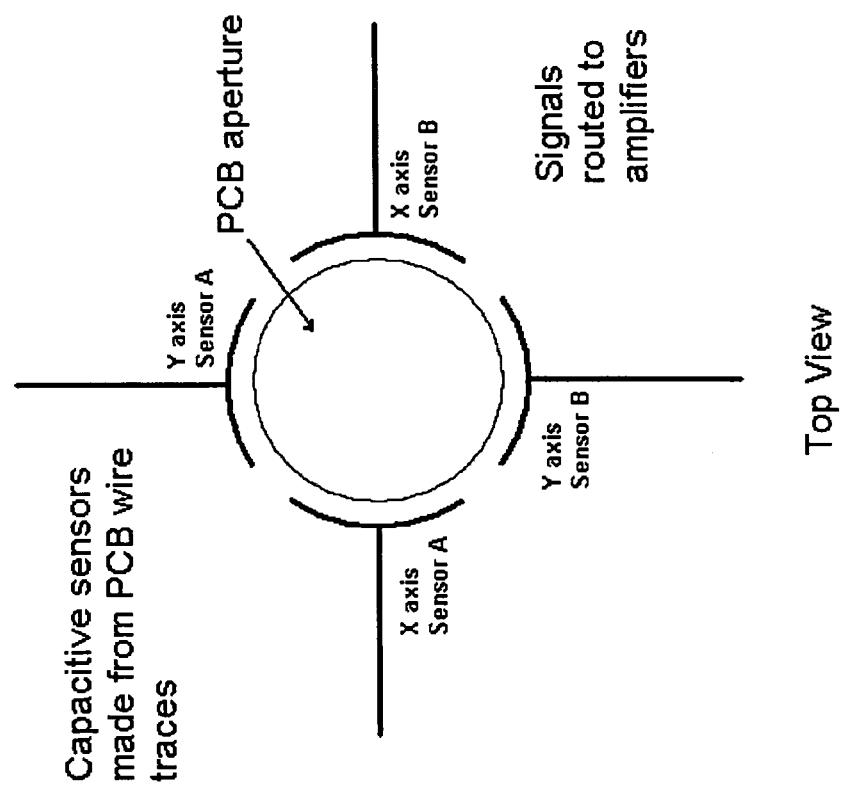
FIG. 3 shows another embodiment for positioning sensors relative to a known location.

Although the FIG. 2 embodiment shows an aperture 204 having a rectangular shape with sensors configured accordingly with two sensors along the x-axis and two sensors along the y-axis, the present methods and systems are not limited to such a configuration, and for embodiments using an aperture, the aperture, and hence the sensors, can be arranged in other numbers and configurations as shown in FIG. 3, for example. Those of ordinary skill will understand that triangular shapes, three dimensional shapes, etc., may be used in locating sensors to allow for sensor detection of the pipette/probe drive signal. Accordingly, it can be understood that for each dimension and/or axes of a coordinate system in which sensors are positioned, at least two sensors in such dimensions/axes can detect the probe/pipette 11 to allow for a positioning and/or alignment of the pipette in such dimension and/or along such axes. As provided herein, in some embodiments, a PCB or other structure providing an aperture may not be used, as the sensors themselves may be positioned to allow for an alignment/positioning of a pipette/probe with a known location. As shown in FIGS. 2 and 3, the sensors in a particular axes, plane, and/or dimension can be aligned substantially symmetrically about the aperture and/or the known location.

Figure 4:
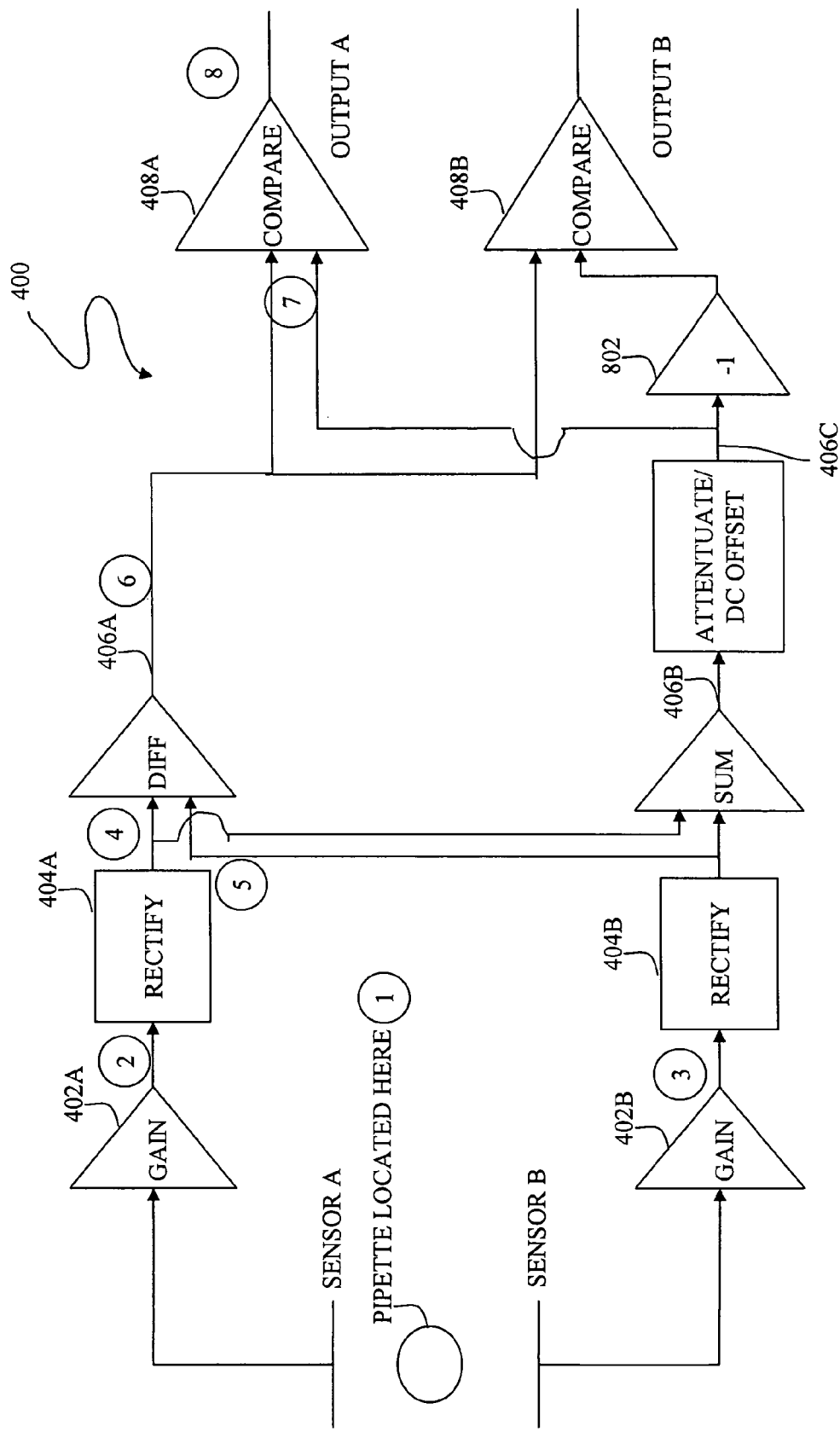
FIG. 4 illustrates one signal processing scheme for processing signals from two sensors.

FIG. 4 shows one embodiment of one type of system 400 that can be used to process signals detected by the sensors of systems such as those according to FIGS. 2 and 3 herein when a probe/pipette is driven with a signal as provided herein. FIG. 4, for example, shows first and second sensors 206A, B which are along an axis of a coordinate system associated with the sensors (and in this example, a known location) and provide a signal, respectively, to amplifiers 402A, B and rectifiers 404A, B which can be full wave or half-wave rectifiers. As further shown, a difference signal 406A and a sum signal 406B can be computed based on the sensor signals. The sum signal 406B can be attenuated and/or a direct current (DC) offset can be applied thereto to provide a processed sum signal 406C, before the difference signal 406A and the processed sum signal 406C are provided to a first comparator 408A, and the difference signal and an inversion of the processed sum signal are provided to a second comparator 408B. As FIG. 4 indicates, the output of the first comparator 408A indicates the distance relative to sensor A 206A, while the output of the second comparator 408B indicates the distance relative to sensor B 206B. In some embodiments where digital comparators are used, a high or logical "one" signal at one of the comparators 408A, B may indicate a relative proximity to a respective sensor, while a low or logical "zero" at both sensors may indicate that the pipette 11 is centered relative to the sensors 206A, B.

The FIG. 4 attenuator can affect the sensitivity of the FIG. 4 detection circuitry. The attenuator can be adjusted to calibrate FIG. 4 system sensitivity to the positioning accuracy and resolution of the positioning/alignment system of the probe/pipette. For example, the attenuator can be viewed as a tolerance that allows for a deviation of the pipette from the "center" of the set of selected sensors (e.g., the centroid of the selected sensors) and/or the known location without requiring correction. The amount of such "deviation" is embodiment-dependent and thus controllable by an attenuator such as that shown in FIG. 4.

Further, the FIG. 4 DC offset can allow for the elimination of noise to cause spurious and/or incorrect adjustments of positioning/alignment during periods when the probe/pipette signal is 0V. Those of ordinary skill will understand that not all systems may employ an attenuator and/or a DC offset as provided in FIG. 4.

As a further consideration and illustration, in an embodiment according to FIG. 4, the capacitive sensors may need calibration due to manufacturing limitations and/or position sensing tolerances, in which case an adjustable gain for each sensor amplifier 402A, B can be provided to allow a probe/pipette midpoint to be found by placing the pipette at the midpoint of a selected sensor set and adjusting the gains until the comparator outputs indicate alignment (e.g., logical zero).

It can thus be understood that detection and/or signal processing "circuitry" or a detection/signal processing scheme/module, an embodiment of which is shown in FIG. 4, can be, but is not limited to, digital, analog, hardware, and/or software, and further, that in some embodiments, a single detection/signal processing module may be used for different dimensions/axes and/or sets of sensors, while in other embodiments, each dimension/axes and/or sensor set may have its own detection/signal processing module. As provided previously herein, the output of the detection/signal processing module(s) can be provided to a processor such as processor 13 for storage of position information/data and/or for providing positional/alignment commands to the probe/pipette 11.

Figure 5:
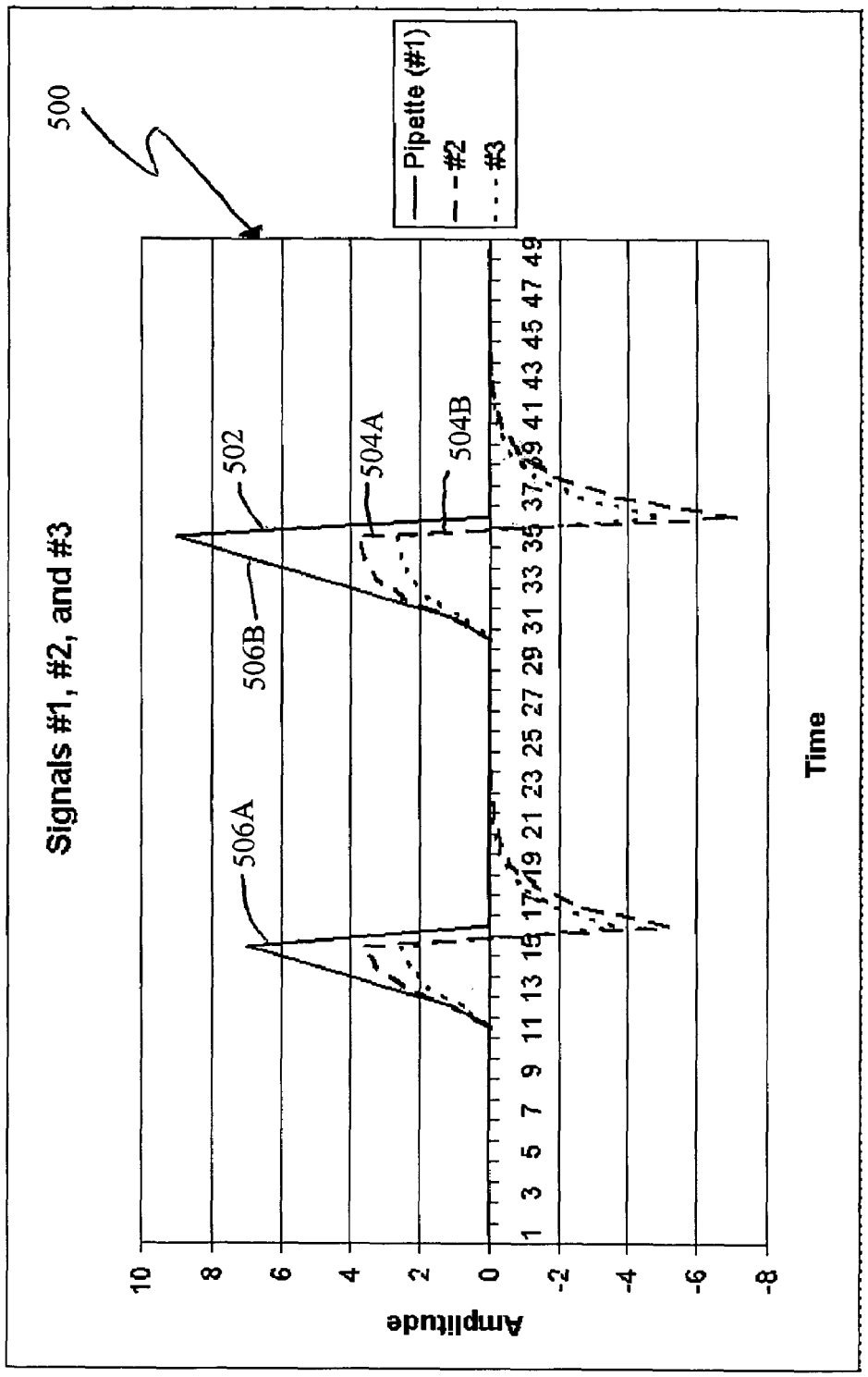
FIG. 5 is a plot showing an example pipette driving signal and representative signals from two sensors.

As an example of the processing scheme of FIG. 4, and with reference to FIG. 2 where a pipette/probe is nearer to x-axis sensor A than to x-axis sensor B, FIG. 5 shows a time versus amplitude plot 500 for a pipette signal 502, a signal based on the signal received at sensor A and amplified thereafter 504A, and a signal based on the signal received at sensor B and amplified thereafter 504B. As FIG. 5 indicates, the pipette signal 502 is a sawtooth signal with the second sawtooth pulse 506B having greater amplitude than the first sawtooth pulse 506A.

It can thus be understood that in the illustrated example, the aforementioned two capacitive sensors detect the pipette signal in differentiated form, where the signal strength detected by each sensor is inversely proportional to the distance between the pipette and each sensor. Accordingly, the smaller the distance between a sensor and the pipette, the greater the capacitance formed by the sensor and pipette. Such relationship can be represented by Equation (1) (ignoring edge effects). Further, the current through a capacitive sensor is dependent upon the capacitance and the derivative of the applied time varying voltage (sourced by the probe/pipette), as shown by Equation (2).

$$C = (A * \epsilon_0)/s \quad (1)$$

$$i = C * dV/dt = (A * \epsilon_0)/s * dV/dt \quad (2)$$

where:
A=area of sensor facing the pipette;
$\epsilon_0$=dielectric constant for the sensor dielectric (e.g., air);
s=distance from a sensor to center of pipette;
V=time varying voltage; and,
t=time.

One of ordinary skill can thus understand that for the illustrated embodiments, the currents at the capacitive sensor outputs can be converted to voltages by the input impedance of the respective amplifiers of FIG. 4, and thereafter amplified thereby. Accordingly, Equations (3) and (4) show a transfer function from the pipette/probe driving voltage 502 through the amplifier stages 506A, B of FIG. 4, where such signals are respectively shown in FIG. 5.

$$V_i = iR \quad (3)$$

$$V_0 = \text{Gain} * V_i \quad (4)$$
$$= \text{Gain} * iR$$
$$= (\text{Gain} * R * A * \epsilon_0)/s * dV/dt$$

where:
$V_i$=input voltage at the amplifier;
$V_0$=output voltage of the amplifier;
Gain=amplifier gain; and,
R=amplifier input impedance.

Based on Equation (4), the signals at the output of the amplifiers 402A, B at points 2 and 3 of FIG. 4 can be described mathematically (ignoring edge effects) by Equations (5) and (6), respectively.

$$V_2 = (\text{Gain} * R * A * \epsilon_0)/s_{PA} * d(V_{pip})/dt \quad (5)$$

$$V_3 = (\text{Gain} * R * A * \epsilon_0)/s_{PB} * d(V_{pip})/dt \quad (6)$$

where:
$s_{PA}$=distance from sensor A to the center of the pipette;
$s_{PB}$=distance from sensor B to the center of the pipette; and,
$V_{pip}$=time varying voltage of the pipette drive.

Figure 6:
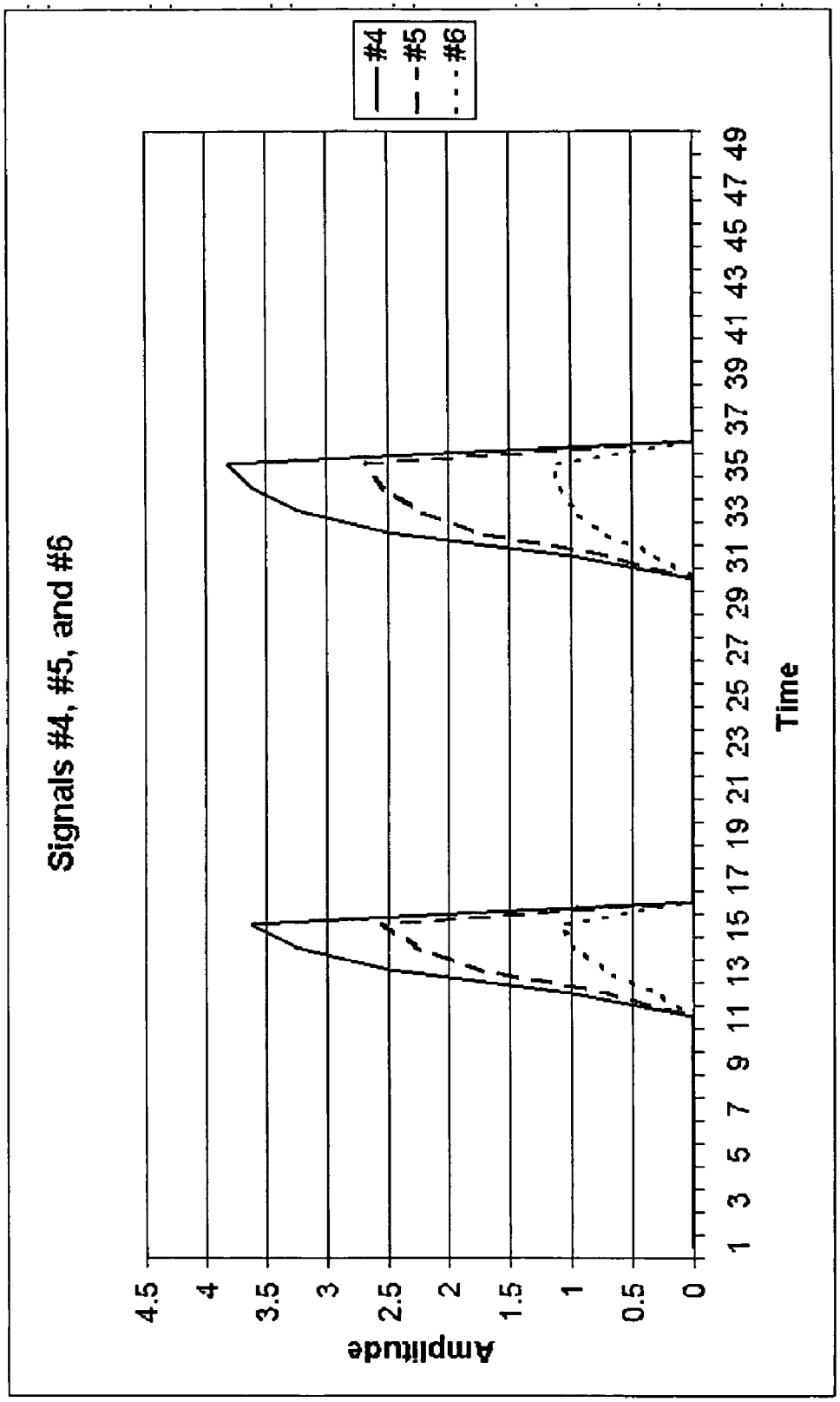
FIG. 6 is a plot showing an example of rectified signals based on the two sensors, and a difference signal based on the two rectified signals.

With continued reference to the FIG. 4 signal processing scheme, as previously indicated, the gain stage outputs are rectified based on the pipette drive waveform, and a sum and a difference signal is computed. Continuing the previous example using the same waveforms, FIG. 6 shows a time versus amplitude plot for the inputs and the output of the difference, shown as points 4, 5, and 6, respectively, in FIG. 4, where half-wave rectified signals are shown. As previously indicated, when the pipette is centered between a capacitive sensor pair (e.g., sensors A and B), the difference signal is substantially zero for a detection system according to FIG. 4. Note that in cases where the two selected sensors are subjected to external noise, the difference amplifier can reduce the noise in the difference signal (i.e., common mode rejection). Equations for the voltage signal at the output of the difference amplifier of FIG. 4 are shown in Equation 7, assuming a full wave rectifier.

$$V_6 = V_4 - V_5$$

$$= abs[(Gain*R*A*\in_0)/s_{PA}*d(V_{pip})/dt] - abs[(Gain*R*A*\in_0)/s_{PB}*d(V_{pip})/dt]$$

$$= abs[(Gain*R*A*\in_0)*d(V_{pip})/dt]*[(1/s_{PA})-(1/s_{PB})] \quad (7)$$

As indicated previously and with continued reference to FIG. 4, the rectified signals are also summed. The previously indicated attenuation and/or DC offset can thus be applied to the sum signal to provide a processed sum signal that can be used as a comparator threshold for the difference signal. By using the processed sum signal as a threshold against which the difference signal can be compared, variations in the amplitude of the pipette signal (e.g., due to pipette signal strength, or external noise in the pipette signal) can be normalized so that such variations do not falsely translate into variations in pipette distance from a sensor. With continued reference to FIG. 4, the voltage at point 7 is presented by Equation 8:

$$V_7 = (V_4 + V_5)/Attenuation$$

$$= \{abs[(Gain*R*A*\in_0)/s_{PA}*d(V_{pip})/dt] + abs[(Gain*R*A*\in_0)/s_{PB}*d(V_{pip})/dt]\}/Attenuation + DC\ Offset$$

$$= \{abs[(Gain*R*A*\in_0)*d(V_{pip})/dt]*[(1/s_{PA})+(1/s_{PB})]\}/Attenuation + DC\ Offset \quad (8)$$

Figure 7:
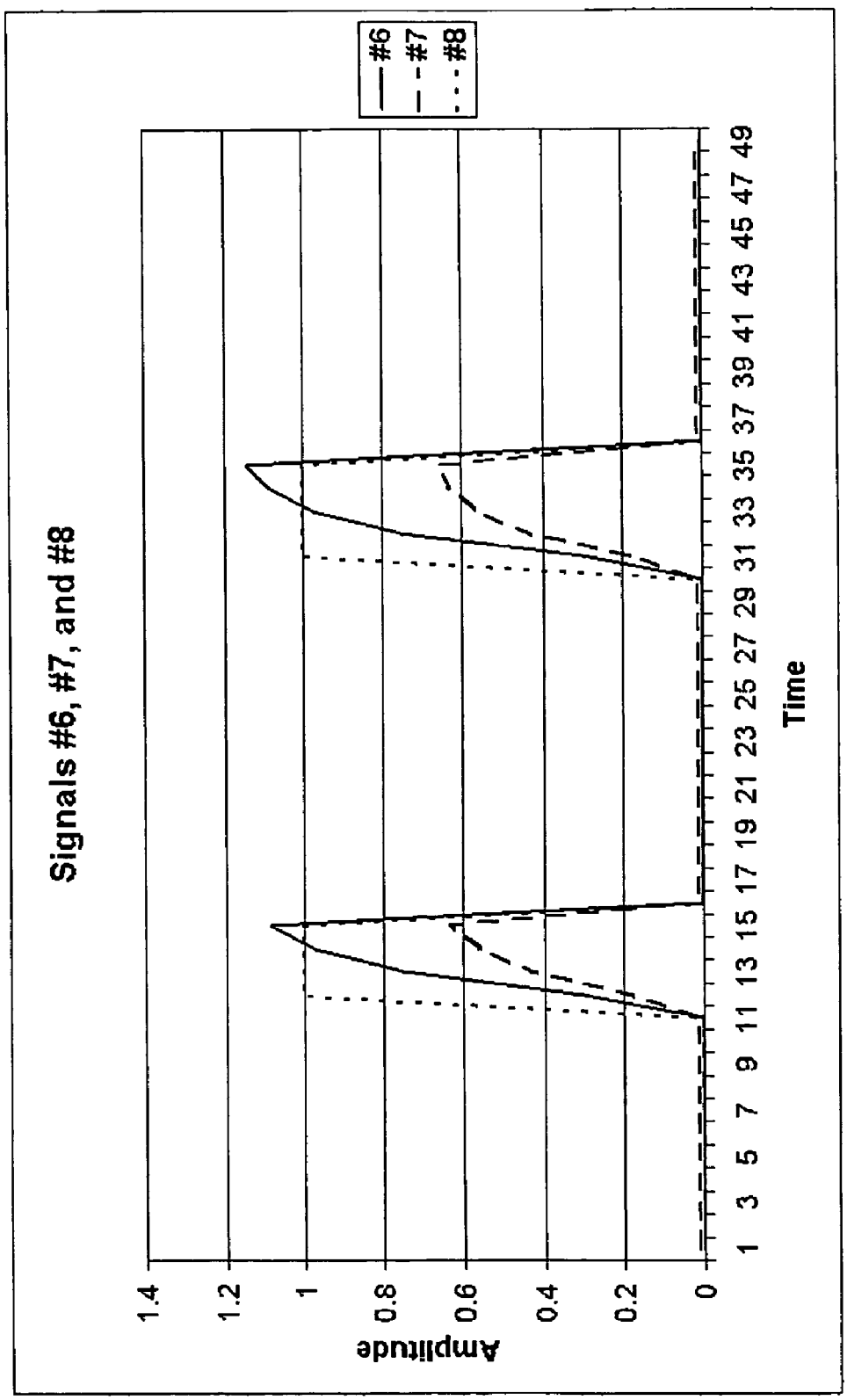
FIG. 7 is a plot showing the difference signal of FIG. 6, a sum signal based on the rectified signals of FIG. 6, and an output of a comparator having the difference signal and the sum signal as input.

When the difference signal is greater than the threshold (e.g., attenuated sum signal+DC offset), the illustrated comparator 408A of FIG. 4 may transition to a logical one, thereby indicating for such system that the pipette is closer to sensor A than sensor B. FIG. 7 shows an example of the signal waveforms at points 6, 7, and 8 of FIG. 4. Equations for the voltage signal at the first comparator output are provided by Equations 9A-C and 10:

When the first comparator 408A provides a logic zero output:

$$V_6/V_7 \leq 1 \quad (9A)$$

$$\{abs[(Gain*R*A*\in_0)*d(V_{pip})/dt]*[(1/s_{PA})-(1/s_{PB})]\}/\{abs[(Gain*R*A*\in_0)*d(V_{pip})/dt]*[(1/s_{PA})+(1/s_{PB})]\}/Attenuation + DC\ Offset\} \leq 1 \quad (9B)$$

Assuming DC Offset is zero, Equation (9B) further reduces to:

$$\frac{[(1/s_{PA})-(1/s_{PB})]}{[(1/s_{PA})+(1/s_{PB})]/Attenuation} \leq 1 \quad (9C)$$

Correspondingly, a "logic one" comparator output at the first comparator 408A is given by Equation 10:

$$\frac{[(1/s_{PA})-(1/s_{PB})]}{[(1/s_{PA})+(1/s_{PB})]/Attenuation} > 1 \quad (10)$$

With continued reference to FIG. 4, the difference signal is input to the second comparator 408B with the attenuated sum signal (multiplied by −1) such that the second comparator 408B provides a logical one output when the pipette is closer to sensor B.

If the distance "d" between two sensors of a sensor pair is known, and if the ratio V6/V7 can be determined using a scheme according to FIG. 4, for example, then $s_{PA}$ and $s_{PB}$ can be computed. By defining $s_{PB}$ in terms of $s_{PA}$ (e.g., $s_{PB}=d-s_{PA}$), and substituting into the ratio for V6/V7 shown by Equations 9 and 10, Equation 11 is obtained:

$$V6/V7 = \frac{[(1/s_{PA})-(1/(d-s_{PA}))]}{[(1/s_{PA})+(1/(d-s_{PA}))]/Attenuation} \quad (11)$$

Solving Equation (11) for the distance SPA yields Equation 12:

$$s_{PA} = d/2*[1-((V6/V7)/Attenuation)] \quad (12)$$

It can be understood that $s_{PB}$ can thereafter be computed from the equation $s_{PB}=d-s_{PA}$. The position of the probe/pipette, including adjustments related thereto to align with the sensors, can thus be made accordingly based on the computed distances (e.g., $s_{PA}$ and $s_{PB}$). It can be understood that the foregoing example is for two sensors in a single direction, and that other embodiments may use multiple sensors in a single direction and/or multiple sensors in multiple planes/directions (e.g., a triangulation scheme, a centroiding scheme, etc.). Further, it can be understood that for a system based on the foregoing Figures, probe positioning may not be performed based on the measurements, as such system may merely use such information to determine the position of a probe based on the distance from the sensors and the known location.

Figure 8:
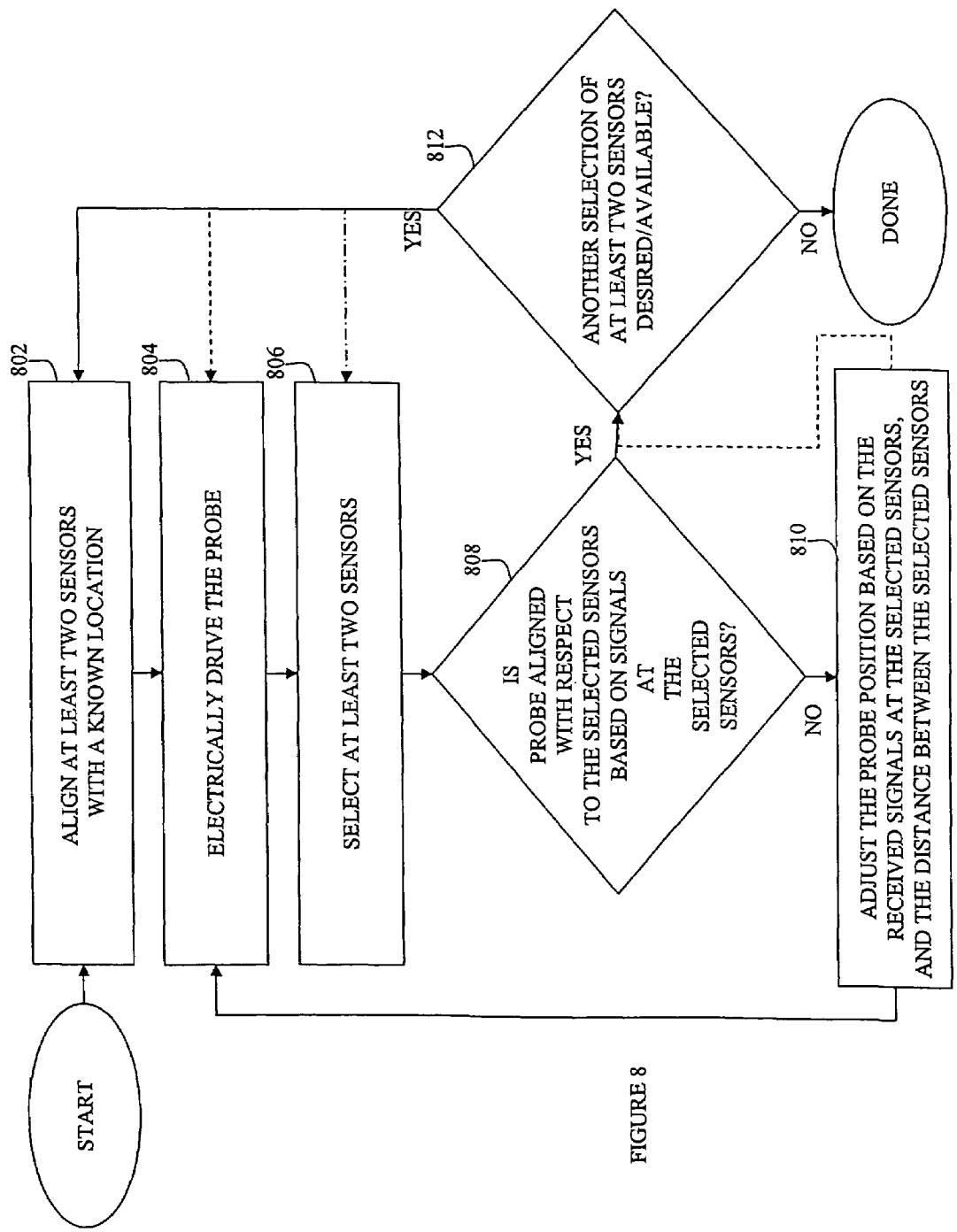
FIG. 8 is a block diagram showing one embodiment of the present methods and systems where a probe is positioned for alignment with a known location; and, FIG. 9 is a block diagram showing one embodiment of the present methods and systems where a probe position is determined based on a known location.
Figure 9:
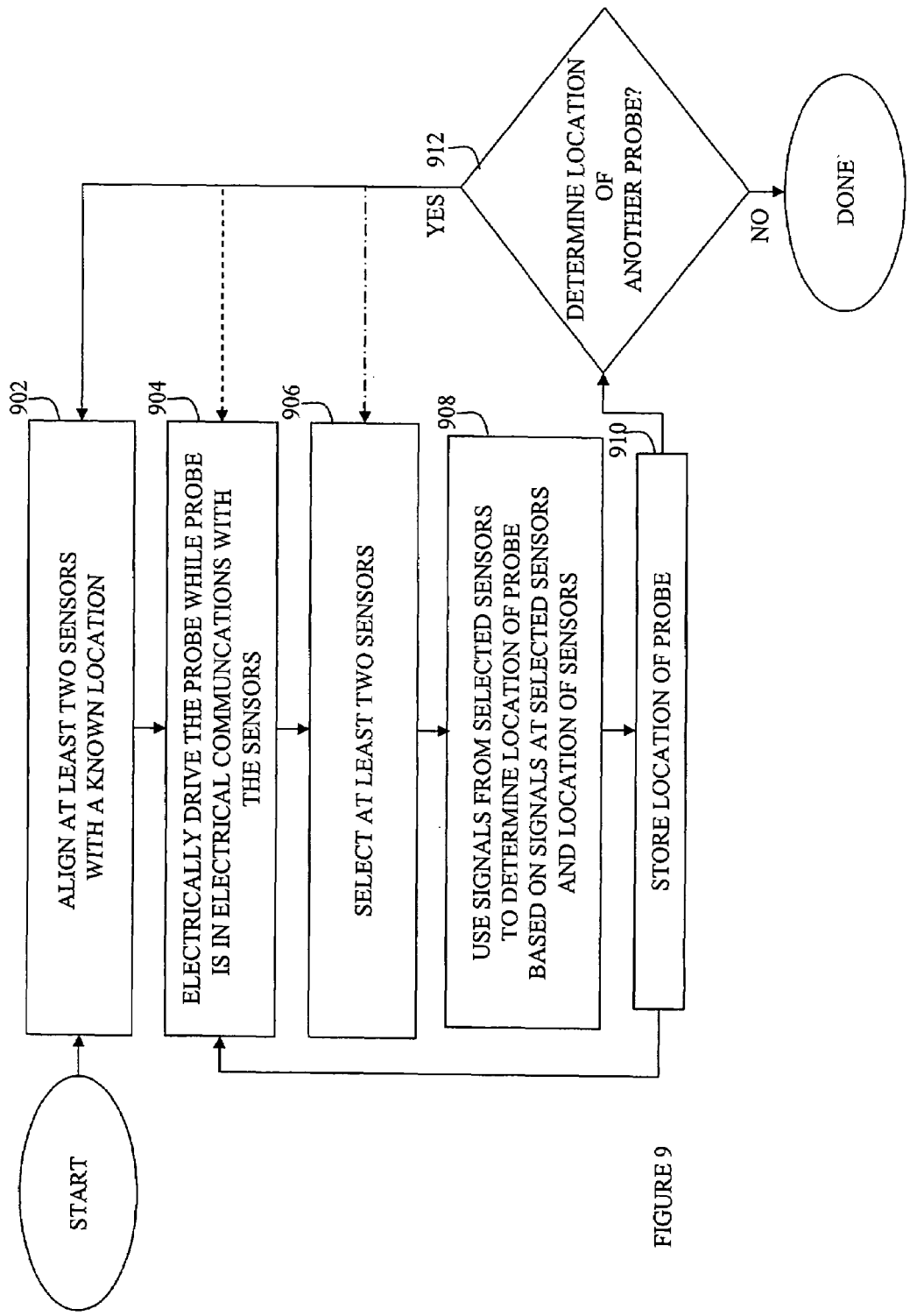

FIG. 8 shows one embodiment for the present methods and systems in which probe alignment and/or positioning with a known location can be performed, while FIG. 9 shows an embodiment where probe position determination is performed. As FIG. 8 indicates, a probe such as a pipette can be positioned and/or aligned with a known location by aligning two or more sensors with a known location such as a well/container location, electrically driving the pipette while the probe is optionally moving towards the known location 804, selecting at least two sensors 806, using the signals received from the selected sensors to determine if an adjustment is needed based on the selected sensors 808 (e.g., in a linear, or multidimensional manner such as triangulation and/or centroiding), adjusting the pipette position/alignment based on the received signals and the location of the selected sensors 810, and thereafter, in embodiments, storing the probe/pipette position (not shown), returning to driving the pipette while optionally moving the probe/pipette towards the known location 804, and making another measurement based on the same selected sensors. In some embodiments, subsequent measurements may include reversing the direction of the pipette to withdraw from the sensors so that another approach towards the sensors (and another measurement(s)) may be made.

In embodiments, once a single positioning/alignment correction is made one or multiple times based on selected sensors (e.g., until the "correction" based on the selected sensors is substantially zero), it may be determined whether other sets of selected sensors are desired for alignment/positioning correction 812. As shown in FIG. 8, if more selected sensor sets are desired, based on the embodiment and the data collected, the methods and systems can return to one of 802, 804, and/or 806 for further positioning/alignment consideration. Once an alignment of a probe/known location is complete, the positioning/alignment information can be stored in a memory for further reference, for example, by a processor as provided previously herein.

FIG. 9 provides an embodiment where probe position can be determined based on the sensor signals and the sensor locations relative to a known position(s). In such an embodiment, as FIG. 9 indicates, two or more sensors can be positioned relative to a known location 902, wherein the probe can be positioned for electrical communication with the sensors. 904. Based on signals received at selected sensors 906 and the positions thereof, the distance between each selected sensors and the probe can be determined (e.g., via triangulation) to provide a probe position 908. Such position can be recorded, for example, in memory 910 for later retrieval, and such process can continue with different known locations and/or different probes 912.

Accordingly, based on FIGS. 8 and 9, in some embodiments, one or more probes/pipettes can be aligned and/or a position determined with one or more known locations and the corresponding data stored in memory for future retrieval. In some instances, the pipette location data can be used to interpolate pipette position to other locations (e.g., other contact points and/or other probe/pipette locations), thereby reducing the need to align each pipette/probe with each known location (e.g., well).

Although in some embodiments, aligning a probe using methods and systems as described herein can be performed using pairs of sensors for a single dimension, it can be understood that some embodiments may perform a multiple dimension technique by selecting at least one pair of sensors in one dimension/axis, correcting the alignment (e.g., FIG. 8) in that dimension, and proceeding to another dimension and repeating, etc. In some of such embodiments, pairs of sensors can be aligned to the known location in multiple dimensions. In further embodiments, as provided herein, multiple sensor selection in multiple dimensions can allow for centroiding, triangulation, etc.

What has thus been described are methods and systems that include aligning at least two sensors with known location, selecting at least two of the at least two sensors, electrically driving the probe, based on signals received by the selected sensors, determining whether the probe is aligned with the known location and/or computing the location of the probe relative to the at least two sensors, and, in some embodiments, adjusting the probe position based on the determination. The methods and systems also include repeatedly returning to electrically driving and positioning the probe until the probe is aligned with the selected sensors, and/or repeatedly returning to selecting at least two of the at least two sensors.

The methods and systems described herein are not limited to a particular hardware or software configuration, and may find applicability in many computing or processing environments. The methods and systems can be implemented in hardware or software, or a combination of hardware and software. The methods and systems can be implemented in one or more computer programs, where a computer program can be understood to include one or more processor executable instructions. The computer program(s) can execute on one or more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) can be implemented using one or more high level procedural or object-oriented programming languages to communicate with a computer system; however, the program(s) can be implemented in assembly or machine language, if desired. The language can be compiled or interpreted.

As provided herein, the processor(s) can thus be embedded in one or more devices that can be operated independently or together in a networked environment, where the network can include, for example, a Local Area Network (LAN), wide area network (WAN), and/or can include an intranet and/or the internet and/or another network. The network(s) can be wired or wireless or a combination thereof and can use one or more communications protocols to facilitate communications between the different processors. The processors can be configured for distributed processing and can utilize, in some embodiments, a client-server model as needed. Accordingly, the methods and systems can utilize multiple processors and/or processor devices, and the processor instructions can be divided amongst such single or multiple processor/devices.

The device(s) or computer systems that integrate with the processor(s) can include, for example, a personal computer(s), workstation (e.g., Sun, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a microprocessor" and "a processor", or "the microprocessor" and "the processor," can be understood to include one or more microprocessors that can communicate in a stand-alone and/or a distributed environment(s), and can thus can be configured to communicate via wired or wireless communications with other processors, where such one or more processor can be configured to operate on one or more processor-controlled devices that can be similar or different devices. Use of such "microprocessor" or "processor" terminology can thus also be understood to include a central processing unit, an arithmetic logic unit, an application-specific integrated circuit (IC), and/or a task engine, with such examples provided for illustration and not limitation. References herein to microprocessor instructions or microprocessor-executable instructions, in accordance with the above, can be understood to include programmable hardware.

Furthermore, references to memory, unless otherwise specified, can include one or more processor-readable and accessible memory elements and/or components that can be internal to the processor-controlled device, external to the processor-controlled device, and/or can be accessed via a wired or wireless network using a variety of communications protocols, and unless otherwise specified, can be arranged to include a combination of external and internal memory devices, where such memory can be contiguous and/or partitioned based on the application. Accordingly, references to a database can be understood to include one or more memory associations, where such references can include commercially available database products (e.g., SQL, Informix, Oracle) and also proprietary databases, and may also include other structures for associating memory such as links, queues, graphs, trees, with such structures provided for illustration and not limitation.

Unless otherwise stated, use of the word "substantially" can be construed to include a precise relationship, condition, arrangement, orientation, and/or other characteristic, and deviations thereof as understood by one of ordinary skill in the art, to the extent that such deviations do not materially affect the disclosed methods and systems.

Throughout the entirety of the present disclosure, use of the articles "a" or "an" to modify a noun can be understood to be used for convenience and to include one, or more than one of the modified noun, unless otherwise specifically stated.

Elements, components, modules, and/or parts thereof that are described and/or otherwise portrayed through the figures to communicate with, be associated with, and/or be based on, something else, can be understood to so communicate, be associated with, and or be based on in a direct and/or indirect manner, unless otherwise stipulated herein.

Although the methods and systems have been described relative to a specific embodiment thereof, they are not so limited. Obviously many modifications and variations may become apparent in light of the above teachings. For example, changes in the details, materials, and arrangement of parts, herein described and illustrated, can be made by those skilled in the art. Accordingly, it will be understood that the following claims are not to be limited to the embodiments disclosed herein, can include practices otherwise than specifically described, and are to be interpreted as broadly as allowed under the law.

What is claimed is:

1. A method for determining the position of a probe, the method comprising:
   distributing an electrical signal to the probe,
   positioning at least two sensors in electrical communication with the electrical signal from the probe,
   generating an electrical signal at the at least two sensors based on electrical communication with the probe, and,
   determining the position of the probe relative to the at least two sensors based on at least one of:
      a sum signal based on the sum of the generated electrical signals at the at least two sensors, and,
      a difference signal based on the difference of the generated electrical signals at the at least two sensors.

2. A method according to claim 1, where determining the position includes determining the position based on the distance between the at least two sensors.

3. A method according to claim 1, where determining the position includes:
   associating the at least two sensors with a coordinate system,
   identifying at least two sensors positioned along at least one of the axes of the coordinate system, and,
   generating at least one of the sum signal and the difference signal based on the respective sum or difference of the generated electrical signals associated with the at least two identified sensors.

4. A method according to claim 3, where the coordinate system is multi-dimensional.

5. A method according to claim 3, where determining the position includes:
   determining the position of the probe by comparing the sum signal and the difference signal.

6. A method according to claim 5, where determining the position of the probe by comparing includes at least one of:
   attenuating the sum signal, and,
   adjusting the DC offset of the sum signal.

7. A method according to claim 5, where determining the position of the probe by comparing includes providing at least one output indicative of which of the identified at least two sensors the probe is nearest.

8. A method according to claim 1, further comprising adjusting the position of the probe based on the determined probe position.

9. A method according to claim 1, where the at least two sensors include a capacitive sensor.

10. A method according to claim 1, where the at least two sensors are in electrical communication with a printed circuit board.

11. A method according to claim 10, where the probe is configured to travel substantially orthogonal to a plane containing the printed circuit board.

12. A method according to claim 10, where the printed circuit board includes an orifice for receiving the probe.

13. A method according to claim 1, where the probe is a pipette.

14. A method according to claim 1, further comprising:
   prior to distributing, aligning the at least two sensors with at least one known location.

15. A method according to claim 1, further comprising:
   extrapolating the determined position to at least one other location in a coordinate system associated with the at least two sensors.

16. A method according to claim 1, further comprising:
   extrapolating the determined position to at least one other location in a coordinate system associated with the probe.

17. A method according to claim 1, further comprising:
   repeatedly returning to distributing until the probe is aligned with the at least two sensors.

* * * * *